United States Patent [19]

Chiu

[11] Patent Number: 4,971,723
[45] Date of Patent: Nov. 20, 1990

[54] PARTIALLY DEBRANCHED STARCHES AND ENZYMATIC PROCESS FOR PREPARING THE STARCHES

[75] Inventor: Chung-Wai Chiu, Westfield, N.J.

[73] Assignee: National Starch and Chemical Investment Holding Corporation, Wilmington, Del.

[21] Appl. No.: 258,231

[22] Filed: Oct. 14, 1988

[51] Int. Cl.$^5$ ............... B01J 13/00; C12P 19/16; A23L 1/0522

[52] U.S. Cl. ................... 252/315.3; 127/39; 127/40; 127/32; 127/71; 435/98; 435/210; 426/578; 426/661; 536/102; 106/213

[58] Field of Search ............ 252/315.3; 435/98, 210; 127/39, 40, 32, 71; 426/578, 661; 536/102

[56] References Cited

U.S. PATENT DOCUMENTS

| | | | |
|---|---|---|---|
| 2,738,305 | 3/1956 | Lohmar, Jr. et al. | 127/71 |
| 2,801,184 | 7/1957 | Miyamoto | 536/102 X |
| 3,532,475 | 1/1972 | Sugimoto et al. | 435/210 X |
| 3,532,602 | 10/1970 | Seidman et al. | 435/98 |
| 3,556,942 | 1/1971 | Hathaway | 435/210 X |
| 3,565,765 | 2/1971 | Heady et al. | 195/31 |
| 3,666,557 | 5/1972 | Jensen et al. | 252/315.3 |
| 3,730,840 | 5/1973 | Sugimoto et al. | 195/31 R |
| 3,766,011 | 10/1973 | Kurimoto et al. | 435/98 X |
| 3,879,212 | 4/1975 | Yoshida | 106/213 |
| 3,881,991 | 5/1975 | Kurimoto et al. | 435/98 X |
| 3,881,991 | 5/1975 | Kurimoto et al. | 127/32 |
| 3,933,196 | 11/1975 | Leach et al. | 195/31 R |
| 3,956,519 | 5/1976 | Evans et al. | 426/570 |
| 4,001,435 | 1/1977 | Hirao et al. | 426/3 |
| 4,113,509 | 9/1978 | Leach et al. | 127/29 |
| 4,211,842 | 7/1980 | Marshall | 435/210 |
| 4,560,651 | 12/1985 | Nielsen et al. | 435/95 |
| 4,726,957 | 2/1988 | Lacourse et al. | 426/578 |
| 4,886,678 | 12/1989 | Chiu et al. | 426/578 |

OTHER PUBLICATIONS

Norman, B. E., "Debranching Enzymes in Dextrose Syrup Production", pp. 157-179 in Maize, *Recent Progress in Chemistry and Technology*, Academic Press, Inc., N.Y., N.Y., (1982).

Slominska, L. et al., *Starch/Starke*, 11:386-390 (1985).

Rutenberg, M. W., "Starch and Its Modifications", pp. 22-36, in *Handbook of Water-Soluble Gums and Resins*, Davidson, Editor, McGraw Hill, Inc., N.Y., N.Y., (1980).

Willox, I. C., et al., *MBAA Technical Quarterly*, 14:105-110 (1977).

Harada, T., *Biotechnology and Genetic Engineering Reviews*, 1:39-63 (1984).

Manners et al., "The Fine Structure of Amylopectin", in *Carbohydrate Research*, 90:99-110 (1981).

Anon., *Bulletin-Leatherhead Food R.A.*, vol. 22, No. 6, Jun. 1988.

*Primary Examiner*—Richard D. Lovering
*Assistant Examiner*—John M. Covert
*Attorney, Agent, or Firm*—Mary E. Porter; Edwin M. Szala

[57] ABSTRACT

This invention provides partially debranched starch, prepared by enzymatic hydrolysis of the alpha-1,6-D-glucosidic bonds of the starch, comprising amylopectin, partially debranched amylopectin and up to 80%, by weight, short chain amylose. This invention also provides a method for preparing this starch, employing an endo-alpha-1,6-D-glucanohydrolase. The starch of this invention is useful for lending a fat-like, lubricating texture to aqueous dispersions, forming stable opaque clouds, forming thermoreversible gels, high strength gels and water-resistant films, and for thickening and bonding.

20 Claims, No Drawings

PARTIALLY DEBRANCHED STARCHES AND ENZYMATIC PROCESS FOR PREPARING THE STARCHES

BACKGROUND OF THE INVENTION

This invention relates to a composition of matter comprising partially debranched starches prepared by enzymatic debranching and to an enzymatic process for preparing the debranched starches.

Starch is a polysaccharide typically comprising a mixture of about 20–25% amylose and about 75–80% amylopectin which is organized into compact granular structures. Amylose is a linear polymer of D-anhydroglucose units which are linked by alpha-1,4-D-glucosidic bonds. Amylopectin is a large branched polymer of amylose chains linked by alpha-1,6-D-glucosidic bonds in a tree-like structure. Depending upon the variety of plant from which the starch is obtained, amylose ordinarily contains between 250 and 12,500 D-anhydroglucose units and amylopectin contains between 400,000 and 3,125,000 D-anhydroglucose units.

Enzymes, or mixtures of enzymes which saccharify and debranch starch, have been used in starch conversion processes for the commercial production of low molecular weight oligosaccharides and sugars, such as dextrose (glucose). Starch conversion is the degradation of starch to lower molecular weight components by treatment with acid, oxidizing agents, heat, alkali or alpha-amylase enzymes. Enzymatic conversion of starch typically involves preferential hydrolysis of the alpha-1,4-D-glucosidic bonds, and only limited, if any, hydrolysis of the alpha-1,6-D-glucosidic bonds.

In the enzymatic conversion of starch to thin-boiling (low viscosity) starch, hydrolysis of branched fragments may be incomplete. For sugar production, however, complete conversion of starch to sugar is desirable, and debranching enzymes have been used to degrade the branched alpha-limit dextrins (branched starch fragments which resist further hydrolysis by alpha-amylase) which remain intact after the enzymatic hydrolysis of alpha-1,4-glucosidic bonds. Glucoamylase, an enzyme which liquifies and saccharifies starch, has been employed for this purpose. Glucoamylase rapidly hydrolyzes alpha-1,4-D-glucosidic bonds and slowly hydrolyzes alpha-1,6-D-glucosidic bonds, releasing glucose. A debranching enzyme, such as pullulanase or isoamylase, which rapidly hydrolyzes only the alpha-1,6-D-glucosidic bonds, releasing short chain amylose, has been suggested for use in conjunction with glucoamylase and alpha-amylase to improve the efficiency of production of high dextrose syrups. These syrups are starting materials in the manufacture of crystalline dextrose and high fructose corn syrup. See Maize, *Recent Progress in Chemistry and Technology*, pp. 157–179, Academic Press, Inc. (1982); and Slominska, L., et al., *Starch/Starke*, 11: 386–390 (1985).

Additionally, debranching enzymes (enzymes which release short chain amylose from starch) have been proposed for use in low calorie alcoholic beverage production to improve fermentability of branched starch fragments; in production of maltose from starch in conjunction with beta-amylase; in low DE maltodextrin (30–55 glucose units) production to induce proteins to aggregate in aqueous emulsions; and in enzymatic conversion of starch into a soluble syrup having a high quantity of disaccharides and trisaccharides. These debranching enzyme applications are directed to problems arising from the presence of branched starch or dextrin fragments following starch conversion processes. In each application, the debranching enzyme is employed in the complete conversion of starch to a variety of low molecular weight fragments such as sugars or maltodextrins. The thickening, adhesion and gelling characteristics of starch are lost.

The use of debranching enzymes to fully debranch starch, with hydrolysis of substantially all alpha-1,6-D-glucosidic bonds, so as to obtain pure, or amylopectin-free, low molecular weight amylose is taught in U.S. Pat. No. 3,730,840 to Sugimoto, et al, U.S. Pat. No. 3,881,991 to Kurimoto, et al, and U.S. Pat. No. 3,879,212 to Yoshida. These patents do not teach the conversion of starch to sugars and other soluble fragments. The object of these patents is to produce pure short chain amylose. The presence of any residual amylopectin is taught to be objectionable.

The background of enzyme-related starch technology does not suggest that useful starch compositions may be prepared by employing debranching enzymes to partially debranch the amylopectin component of the starch, yielding a mixture of short chain amylose, amylopectin and partially debranched amylopectin, with or without substantial conversion of the starch. The functional properties of the partially debranched starch of this invention are novel. Furthermore, nothing in the literature suggests the utility of an enzymatic process for partially debranching starch as a replacement, in whole, or in part, for processes that are commercially used to produce various modified starches. The enzymatic process offers significant advantages over other processes, particularly in food and cosmetic applications where the demand for "natural" products persists.

It is an object of this invention to provide starches which are partially enzymatically debranched and which possess a variety of properties which the untreated, branched starches do not possess. These properties are in addition to the expected rheological properties (i.e., thickening and adhesion) for which starches have traditionally been employed. These properties include, but are not limited to, fat-like textures ranging from oily to creamy to waxy, stable cloud formation, cold-water insoluble film formation, high strength gel formation, and thermoreversible gel formation in aqueous dispersions. A thermally reversible starch gel is one which melts upon heating and reforms upon cooling. Gels prepared from unmodified starches are not thermally reversible.

It is a further object of this invention to provide an enzymatic process for producing these starches, employing an alpha-1,6-D-glucanohydrolase, such as pullulanase, isoamylase or amylo-1,6-glucosidase.

SUMMARY OF THE INVENTION

This invention provides partially debranched starches. This invention also provides an enzymatic process for preparing these starches. The starches may be used to lend fat-like texture to aqueous dispersions, form thermoreversible gels, form high strength gels, form films, form stable clouds, thicken, bond, stabilize and replace derivatized and other modified starches in many applications.

The partially debranched starches comprise a mixture of partially debranched amylopectin, short chain amylose, and, optionally, amylopectin in proportions which are adjusted for particular applications by controlling the degree of debranching and the selection of starch source. Starches from many sources, such as corn, which contain long chain amylose, retain their long chain amylose content following enzyme treatment. Starches from any source may be employed in this invention. Depending on the end use and the starch source selected, the starch may be debranched by treatment with a alpha-1,6-D-glucanohydrolase until up to 80%, by weight of the starch, has been debranched to short chain amylose.

The enzymatic treatment utilized in the process of this invention may be carried out on any pregelatinized starch which contains alpha-1,6-D-glucosidic bonds. In preparing the partially debranched starch, the starch is selected from an appropriate source and slurried in water. The mixture is then cooked to gelatinize the starch. If desired, the starch may be used in the granular form, but enzymatic degradation of granular starch proceeds slowly. The temperature and pH of the mixture are adjusted to the optimum for the particular enzyme to be used, and the slurry is then brought into contact with the enzyme.

The enzyme must be an endo-enzyme, capable of hydrolyzing the alpha-1,6-D-glucosidic linkages of the starch molecule, and incapable of any significant degree of hydrolysis of the alpha-1,4-D-glucosidic linkages. Pullulanase, which is preferred, is a very specific endo-enzyme which, by its action, is able to form a reaction complex only with alpha-1,6-D-glucosidic bonds located adjacent to a chain of alpha-1,4-D-glucosidic bonds. Because this endo-enzyme is capable of hydrolyzing the 1,6-linkages of the starch molecule but incapable of hydrolyzing the 1,4-linkages, the residue of such a debranching procedure is a complex mixture which invariably contains a higher proportion of linear to branched chain molecules than the starting material. Thus, the composition and properties of partially debranched starches do not resemble those of converted starch products (i.e., thin-boiling starches, oligosaccharides, sugars and dextrins), nor those of fully debranched starch products (i.e., short and long chain amylose).

The enzyme is permitted to digest the starch until up to about 80%, by weight, of the starch has been debranched to short chain amylose, or until the desired end point (i.e., sufficient debranching to provide the desired functional properties) has been reached. Ordinarily the degradation will be carried out for periods ranging up to 24 hours, or more, depending on the temperature, enzyme and substrate concentrations, and other process variables. The enzyme degradation is then terminated by means of heat, chemical addition, or other methods known in the art for deactivating enzymes. The partially debranched starch composition may be spray dried, drum dried or otherwise recovered in a form suitable for its intended use.

DESCRIPTION OF THE PREFERRED EMBODIMENTS

The starches which may be used in preparing the enzyme degraded starch herein may be derived from any source, including corn, potato, sweet potato, wheat, rice, sago, tapioca, waxy maize, sorghum, and the like. Also included are the conversion products derived from any of the above starches, including fluidity or thin-boiling starches prepared by oxidation, alpha-amylase conversion, mild acid hydrolysis or heat dextrinization. Derivatized starches such as ethers and esters and other modified starches may also be employed.

The starch will preferably be a gelatinized starch (a precooked, cold-water-swelling starch) and also may be a fluidity starch converted by mild acid degradation, heat dextrinization, or any one of several methods that are well known in the art. See, e.g., M. W. Rutenberg, "Starch and Its Modifications" P. 22–36, in *Handbook of Water-Soluble Gums and Resins*, R. L. Davidson, editor, McGraw Hill, Inc., New York, N.Y., 1980. If desired, the starch may be converted by treatment with an alpha-amylase to produce a fluidity starch in the manner disclosed in U.S. Pat. No. 4,726,957 to Lacourse, et al. A combination of one or more of these conversion techniques may be used. The conversion is typically carried out before derivatization or crosslinking, but may be carried out before or after the enzymatic treatment. Where a high viscosity debranched starch is desired, it is not desirable to convert the starch.

Where a low viscosity starch is desirable, a starch, such as waxy maize, which has been converted to a Water Fluidity (WF) of up to about 60 is preferred. Water Fluidity is an empirical measure of viscosity on a scale of 0–90, wherein fluidity is the reciprocal of viscosity.

For other products, derivatization to any degree of substitution or level of conversion that results in the desired viscosity and functional characteristics may be employed prior to, or following, enzymatic debranching. For example, if the debranched starch is employed as an emulsifying agent in foods, an octenylsuccinate derivative (OSA starch) is preferred. The starch is treated with octenylsuccinic acid anhydride to form a starch ester derivative containing from 0.25 to 3.0%, by weight, of octenylsuccinate.

In a preferred embodiment, the next step after preparing the starch derivative is to heat an aqueous dispersion of the derivatized starch to gelatinize the derivatized starch. The gelatinization process disrupts, in whole or in part, the associative bonding of the starch molecule within the raw starch granule, thereby making the molecule more accessible to the enzyme and permitting the enzyme to more easily and uniformly debranch the starch molecules. After a slurry of the starch has been gelatinized, the solids, temperature and pH of the dispersion are adjusted to provide optimum enzyme activity.

The optimum parameters for enzyme activity will vary depending upon the enzyme used. Thus, the rate of enzymatic debranching depends on factors including enzyme concentration, substrate concentration, pH, temperature, the presence or absence of inhibitors and other factors. Depending on the type of enzyme, or its source, various parameters may require adjustment to achieve optimum debranching rate. In general, enzymatic debranching is carried out at the highest feasible solids content to facilitate subsequent drying of the starch while maintaining optimum debranching rates. For example, for the pullulanase used herein to produce a starch suitable for use as a fat replacer, a precooked starch dispersion ranging up to 28% solids is preferred.

The practitioner will recognize that a higher solids starch system (e.g., above 50% solids) may be employed if the starch is gelatinized with a process which produces adequate mixing to uniformly blend the enzyme and the starch at higher solids. The practitioner will also recognize that the temperature, treatment time and other parameters of the enzymatic debranching process must be adjusted to the higher solids content. Processes which employ higher solids starch dispersions are intended to fall within the scope of this invention and may be used to prepare the modified starch herein.

Although the process of this invention is primarily illustrated by employing pullulanase (E.C. 3.2. 1.41; pullulan 6-glucanohydrolase) as the enzyme component, other endo-alpha-1,6-glucanohydrolases, such as isoamylase (E.C. 3.2. 1.68), or any other endo-enzyme which exhibits selectivity in cleaving the 1,6-linkages of the starch molecule, leaving the 1,4-linkages substantially intact and releasing short chain amylose, may be used to prepare the debranched starch herein.

In a preferred embodiment, the enzyme used is a heat stable pullulanase obtained from a novel species of *Bacillus*. This pullulanase will catalyze the hydrolysis of the alpha-1,6 linkages in pullulan and amylopectin, provided that there are at least two glucose units in the side chain. Pullulanase is a linear polymer consisting essentially of D-glucopyranosyl triose units joined by alpha-1,6 linkages.

Optimum concentrations of enzyme and substrate are governed by the level of enzyme activity which will vary depending upon the enzyme source, the enzyme supplier and concentration of the enzyme provided in commercially available batches. Although the process of this invention makes use of an enzyme in solution, processes utilizing an enzyme immobilized on a solid support are intended to fall within the scope of this invention.

The reaction may proceed in the presence of buffers to ensure that the pH will be at the optimum level throughout the degradation. Buffers such as acetates, citrates, or the salts of other weak acids are acceptable. Other agents may be used to optimize enzyme activity. The reaction may be carried out in a pH range from about 3.0 to 7.5, with the preferred range being between 4.5 and 5.5, and the optimum being 5.0 when the temperature is 60° C. and the enzyme is the *Bacillus* pullulanase.

The aqueous starch dispersion should be held during the enzymatic debranching at a temperature of about 25°–100° C., the preferred range being 55°–65° C. and the optimum being 60° C. at pH 5.0 for the *Bacillus* pullulanase. However, if shorter treatment times are desired, a temperature range from 60°–65° C. or a higher enzyme concentration may be used. Alternatively, a higher temperature may be employed if a thermally stable debranching enzyme which yeilds short chain amylose from starch is selected for use herein. As with other parameters of the enzyme reaction, the preferred and optimum temperature ranges will vary with changes in other parameters such as substrate concentration, pH and other factors affecting enzyme activity, and can be determined by the practitioner.

The enzymatic treatment is permitted to continue until the desired level of debranching is reached. The progress of the enzymatic treatment may be measured by various methods. If all critical parameters have been established for achieving a particular starch composition, then the treatment may be allowed to proceed to a predetermined relative end point in time. The end point may be determined by change in viscosity, by gel permeation chromatography, by reducing group content, iodine reaction or by any other method known in the art for measuring the degree of enzymatic debranching of the starch molecule.

In a preferred embodiment, the debranching end point is measured by determining the viscosity of a starch dispersion at 72° F. using the funnel viscosity method set forth in Example 1, below. The funnel viscosity method is a rapid, simple method for determining viscosity, in which the amount of time needed for a standard quantity of starch slurry to flow through a standard size funnel is recorded.

In a second preferred embodiment, the degree of starch debranching is measured by gel permeation chromatography. After separating the starch into its different molecular weight fractions, the percentage of short chain amylose is determined by calculating the percentage, by weight, of the low molecular weight fraction of the partially debranched starch. It will be understood by the practitioner that these percentages are approximately equal to the amount of short chain amylose which has been liberated from the amylopectin by the debranching enzyme. Experimental error in gel permeation chromatography (e.g., due to contamination by the enzyme, or by sugars or dextrins introduced with the starch, the enzyme solution, the buffer or other process components) may result in a percent low molecular weight fraction which may range up to 5% more than the percent short chain amylose of the starch sample.

The degree of starch debranching needed for a particular application depends on the type of starch utilized, the presence and nature of any substituent groups and the degree, if any, of conversion. The practitioner will be able to select a suitable starch and determine the necessary debranching for any particular end-use with a minimum of experimentation.

While any amylopectin-containing starch may be employed, the effects of partial enzymatic debranching will be more dramatic as the amylopectin content increases. Thus, although all commercially available starches may be employed herein, waxy maize which contains about 100% amylopectin, is preferred. Up to 80% of the waxy maize starch may be debranched to short chain amylose. Less than 80% of other starches may be debranched and the debranching must be controlled so that at least 20% partially debranched amylopectin remains.

In a preferred embodiment, waxy maize starch, or some other waxy starch (e.g., waxy rice or barley starch), is partially debranched, yielding sufficient short chain amylose to form a thermally reversible gel in an aqueous starch dispersion. The starch comprises from 25 to 70% short chain amylose, and preferably, from 35 to 65% short chain amylose. The same degree of debranching of waxy starches is preferred for lending a fat-like, lubricating texture to an aqueous starch dispersion. Converted waxy starches (e.g., 50 WF acid-converted waxy maize or waxy rice) are also preferred for preparing a thermally reversible gel and providing fat-like qualities in an aqueous starch dispersion.

For preparing high strength starch gels, partially debranched corn starch, comprising 10 to 45% short chain amylose, and preferably 15 to 40% short chain amylose, is preferred.

For preparing water-insoluble films, the preferred amount of debranching decreases as the long chain amylose content of the starch increases. For potato starch, at least 20% short chain amylose must be provided. For tapioca starch, at least 25% short chain amylose, and for waxy maize starch, at least 35% short chain amylose, is preferred.

For preparing a stable, opaque cloud in an aqueous starch dispersion, unmodified or converted debranched waxy starches are preferred. For waxy maize starch, debranching is continued until 20 to 65%, and preferably 30 to 65%, short chain amylose has been produced. For acid-converted waxy maize starch, debranching to yield from 30 to 55% short chain amylose is preferred.

After the desired degree of starch debranching has been reached, the enzyme may be deactivated. Pullulanase is rapidly deactivated at temperatures above about 70° C., therefore, the reaction may be conveniently terminated by increasing the temperature of the starch dispersion to at least 75° C. for about 15 minutes.

If the end-use application requires purification of the starch, the reaction impurities and by-products may be removed by dialysis, filtration, ion exchange processes, centrifugation or any other method known in the art for isolating and recovering the starch.

If a dried starch is desired for end use applications, the starch may be dehydrated by any method known in the art.

It is to be understood that the invention includes any starch blend which contains partially debranched starch. Thus, this invention includes blends of partially debranched starch and other components, such as chemically modified starches and other polymers, and includes multi-step processes in which an enzyme is employed in one step to partially debranch starch. For example, this invention includes multi-step processes and starch blends wherein the starch is converted, derivatized, crosslinked or otherwise modified in addition to being subjected to partial enzymatic debranching.

The following examples will more fully illustrate the embodiments of this invention. In these examples, all parts and percentages are given by dry weight basis and all temperature are in degrees Celsius unless otherwise noted.

EXAMPLE 1

This example illustrates the preparation of representative partially debranched starches by the process of this invention.

The starches were converted, derivatized or crosslinked, where applicable, prior to gelatinization and treatment with pullulanase. To convert the starch, a slurry of 100 parts of starch in 150 parts of water was heated to 52° C., the indicated amount of hydrochloric acid (1.75%) was added, and the mixture was stirred for 16 hours at 52° C. The hydrolysis was stopped by neutralizing the mixture with alkali (a solution of 3% sodium hydroxide) to a pH of 5.5. The converted starch was recovered by filtration, washed and dried.

STARCH DERIVATIZATION

To prepare the octenylsuccinate derivative, 100 parts of starch was slurried in 150 parts water, the pH was adjusted to 7.5 with sodium hydroxide, and the indicated amount of octenylsuccinic anhydride was added slowly while the pH was maintained at 7.5 with the alkali. The reaction was complete when no further addition of alkali was necessary. The pH was adjusted to between 4.0 and 6.5 and the resulting derivatives were recovered by filtration, washed and dried.

To prepare the acetate derivative, 100 parts of the starch was slurried in 150 parts water, adjusting the pH to 8.3 with 3% sodium hydroxide solution, and slowly adding the indicated amount of acetic anhydride while maintaining the pH at 8.3 with the above alkali. The reaction was complete when no further addition of alkali was necessary. The pH was adjusted to between 4.0 and 6.5 and the resulting derivative was recovered as above.

The crosslinked starch was prepared by slurring 100 parts of starch in 150 parts water, adding 0.8 part sodium hydroxide, 1.0 part sodium chloride, and then adding the indicated amount of phosphorus oxychloride. The slurry was agitated for 3 hours at room temperature. When the reaction was completed, the pH was adjusted to 5.5 with acid. The starch was recovered by filtration, washed, and dried.

STARCH DEBRANCHING

An aqueous slurry (20-30% solids) was prepared employing the desired starch. The aqueous starch slurry was jet-cooked at approximately 300° F. (149° C.) to gelatinize the starch. The cooked starch dispersion was placed in a constant temperature bath at 58°-60° C. with constant stirring. The pH was adjusted to 5 with 3% hydrochloric acid.

Depending on the type of starch used and its amylopectin content, between 0.5 and 10.0 mls of pullulanase per 100 g of starch were added to the cooked starch dispersion. The pullulanase (E.C. 3.2.1 41, pullulan 6-glucano-hydrolase) which was used is produced by a novel species of *Bacillus*. This enzyme (Promozyme TM) was obtained from Novo Industri A/S of Denmark. The enzymatic activity of Promozyme in a 1.25 g/ml solution is standardized at 200 PUN/ml of solution. One PUN (Pullulanase Unit Novo) is the amount of enzyme which, under standard conditions, hydrolyzes pullulan, liberating reducing carbohydrate with a reducing power equivalent to 1 micro-mol glucose per minute. The procedure for determining PUN is available from Novo Industri A/S.

Thus, in the starch dispersion employing corn starch, 125 PUN of pullulanase per 100 g corn starch was added to the dispersion. For the waxy maize starch slurry (with higher amylopectin content), 750 PUN of pullulanase per 100 g waxy maize starch was added to the dispersion.

The amount of debranching was measured intially by the funnel viscosity test and subsequently by gel permeation chromatography.

FUNNEL VISCOSITY MEASUREMENT

To measure funnel viscosity at 19% solids, 38 g of the starch (anhydrous basis) was weighed into a tared 250 ml beaker (stainless steel) containing a thermometer and brought to 200 g total weight with distilled water. The sample was mixed to dissolve any lumps and heated or cooled to 72° F. (22° C.). A total of 100 ml of the cooked starch dispersion was measured into a graduated cylinder. It was then poured into a calibrated funnel while using a finger to close the orifice. A small amount was allowed to flow into the graduate to remove any trapped air, and the complete balance remaining in the graduate was poured back into the funnel. Using a timer, the time required for the 100 ml sample to flow through the apex of the funnel was recorded.

The funnel was a standard 58°, thick-wall, resistance glass funnel whose top diameter was about 9-10 cm with the inside diameter of the stem being about 0.381 cm. The funnel was calibrated so as to allow 100 ml of water to go through in 6 seconds using the above procedure.

CORN STARCH (CAUSTIC) FUNNEL VISCOSITY

Due to retrogradation of the starch which occurs when using corn starch, the funnel viscosity measurement was modified as follows for debranched corn starch:

1. the starch sample weight was reduced to 15 g (anhydrous basis);
2. sufficient hot (at least 90° C.) water was added to the starch to bring it to 150 g total weight;
3. 15 g of 25% w/v sodium hydroxide solution was added to the hot starch slurry; and
4. with stirring, the slurry was cooled to 72° F. and the measurement carried out as set forth above.

GEL PERMEATION CHROMATOGRAPHY

Starches were prepared for analysis by slurrying 5 mg of starch in 4 ml of dimethylsulfoxide ("DMSO") containing 0.03M sodium nitrate and heating the slurry to 80° C. for at least 30 minutes to dissolve the starch. Samples (200 μl) were injected into an ALC/GPC-150C Chromatograph (Waters Associates, Milford, Mass.) (equipped with a Nelson 3000 Series Chromatography Data System and two PLgel mixed 10 μm columns (obtained from Polymer Laboratory, Amherst, Mass.), employing DMSO containing 0.03M sodium nitrate as the mobile phase) and eluted at a rate of 1 ml/min. The columns were calibrated using dextran standards (with molecular weights of 2,000; 20,000; 80,000; 500,000; and 2,000,000, obtained from Pharmacia Fine Chemicals, Piscataway, N.J.). The percentage short chain amylose was calculated from the relative area of the peak obtained within the molecular weight range from 500 to 20,000.

PREPARATION OF DEBRANCHED OSA WAXY MAIZE STARCHES

Employing the process set forth above, an OSA starch derivative was prepared by reacting 4,000 g of waxy maize starch with 1% octenylsuccinic anhydride. The starch was then jet cooked at pH 5.0 to yield a 23% starch dispersion. Pullulanase (80 mls) was added to the dispersion at 58° C. with aggitation. After 24 hours, the funnel viscosity was 35 seconds at 19% solids and 72° F.

The debranching was continued by adding an additional 80 mls of pullulanase at 58° C. and aggitating the dispersion for an additional 3 hours. The pullulanase was deactivated by heating the dispersion to about 80° C. The funnel viscosity was 12 seconds at 19% solids and 72° F. The starch dispersion was spray dried at an inlet temperature of 200°–210° C. and an outlet temperature of 80°–90° C. The spray-dried starch was screened through #40 mesh screen.

A second sample of OSA waxy maize starch (4,000 g) was prepared and debranched in the same manner as the first sample, except that 20 mls of pullulanase was employed in a single addition. Debranching continued for two hours at which time the funnel viscosity was 50 seconds at 10% solids and 72° F. This sample was spray-dried in the same manner as the first sample.

EXAMPLE 2

This example illustrates the preparation of partially debranched starch employing the enzyme isoamylase (glycogen 6-glucano-hydrolase; E.C. 3.2.1.68).

A cooked, 24% solids, aqueous dispersion of waxy maize starch (2,500 g) was treated with 5,000 units of a *Pseudomonas amyloderamosa* isoamylase (obtained from Sigma Chemical Company, St. Louis, Mo.). One unit of this isoamylase causes an increase in absorbance ($A_{610}$) of 0.1 in 1 hour using rice starch as a substrate.

The starch dispersion was heated to 45° C. at pH 4.0, the enzyme was added and the mixture was stirred for 26 hours. A portion of the mixture was removed, heated to 80° C. to deactivate the enzyme, and spray-dried and screened as in Example 1. The remaining portion of the starch mixture was enzymatically treated for a total of 43 hours, at which time the enzyme was deactivated and the starch dried and screened as above.

The quantity of short chain amylose obtained from isoamylase hydrolysis was measured with gel permeation chromatograpy. The 26 hour sample contained 21.9% and the 43 hour sample contained 28.4% short chain amylose.

EXAMPLE 3

This example illustrates the relationships between treatment time, funnel viscosity (or Water Fluidity) and percentage short chain amylose of the starches of this invention.

The partial enzymatic debranching process of Example 1 was carried out on the starches listed in Table I.

The funnel viscosity and percent short chain amylose were measured by the methods set forth above. Results are shown in Table I.

TABLE I

| Starch | Treatment Time (hrs.) | Funnel Viscosity (seconds) | % Solids | % Short Chain Amylose |
|---|---|---|---|---|
| Waxy-Maize Acid-Converted to 50 WF | | | | |
| 1 | 0.5 | 110 | 19 | 13.5 |
| 2 | 1.0 | 22 | 19 | 26.3 |
| 3 | 20.0 | 20 | 19 | 27.1 |
| 4 | 20.0 | 18 | 19 | 31.8 |
| 5 | 25.0 | 14 | 19 | 35.1 |
| 6 | 44.0 | 12 | 19 | 48.0 |
| Waxy-Maize | | | | |
| 1 | 0.25 | 110 | 19 | 22.1 |
| 2 | 1.0 | 52 | 19 | 23.8 |
| 3 | 20.0 | 20 | 19 | 32.6 |
| 4 | 20.0 | 16 | 19 | 40.0 |
| 5 | 24.0 | 12 | 19 | 45.6 |
| 6 | 45.0 | 12 | 19 | 51.9 |
| Corn[a] | | | | |
| 1 | 1.0 | 97 | 10 | 14.5 |
| 2 | 3.0 | 37 | 10 | 21.9 |
| 3 | 5.0 | 30 | 10 | 26.5 |
| 4 | 7.0 | 27 | 10 | 24.9 |
| 5 | 24.0 | 18 | 10 | 33.3 |
| 6 | 48.0 | 12 | 10 | 47.5 |

[a]Caustic Funnel Viscosity.

The results show generally that as reaction time increases, the percent short chain amylose increases and the funnel viscosity decreases in a non-linear fashion. Thus, one or more of these measurements may be employed to measure the progress of the enzymatic debranching.

EXAMPLE 4

This example illustrates that the starch of this invention may be used to create lubricity and fat-like texture in an aqueous starch dispersion.

A waxy maize starch was partially debranched by the method of Example 1 to a funnel viscosity of 10–12 seconds at 72° F. and 10% solids (about 50% short chain amylose).

Fat-like or lubricating properties of the starch were evaluated by dispersing 25 g, anhydrous, of starch in 75 g of distilled water. The dispersion was heated on a steam bath for 20 minutes, poured into a petri dish, refrigerated for one hour and subjectively evaluated. The partially debranched starch gel was spread on the palm of the hand and observed to have a lubricating, creamy touch. The gel was glossy and opaque.

distilled water at 1.0% solids and the transmittance of the dispersion was measured.

The percent light transmittance of a 1% solids starch dispersion in distilled water (0.2% solids for tapioca) was measured initially and after 24 hours using a Brinkman P.C. 800 Colorimeter. Results are set forth in Table II. As the cloud forming capacity of the starch improved, the percent light transmittance decreased. A significant increase in percent light transmittance after 24 hours indicates the starch cloud was not stable.

TABLE II

| Starch[a] | Funnel Viscosity (seconds) | % Solids | % Short Chain Amylose | % Transmittance[b] Initial | After 24 Hrs. |
|---|---|---|---|---|---|
| Waxy Maize | | | | | |
| A | 96 | 10 | — | 20 | 23 |
| B | 27.6 | 10 | 13.5 | 22 | 25 |
| C | 13.0 | 19 | 40 | 3.0 | 10.4 |
| D | 11.7 | 19 | 45 | 0.8 | 1.5 |
| Acid-Converted (50 WF) | | | | | |
| E | 20.6 | 19 | 26.5 | 3.9 | 10.2 |
| F | 10.2 | 19 | 50 | 3.0 | 8.2 |
| G | 7.0 | 19 | over 60 | 0.9 | 77 |
| Tapioca | 54.0 | 10 | 13 | 9 | 23 |
| Fully Debranched (U.S. Pat. No. 3,730,840) | — | — | 84 | 1 | 60 |

[a]See Example 7.
[b]Some precipitate was observed in samples showing an increase in light transmittance after 24 hours.

EXAMPLE 5

This example illustrates that the starch of this invention may be used in film forming applications.

A waxy maize starch was partially debranched to a funnel viscosity of 10 seconds at 72° F. and 19% solids (about 50% short chain amylose) by the method set forth in Example 1. An acid-converted (85WF) waxy maize starch (approximately the same viscosity as the debranched starch) was compared to the debranched starch.

A film was prepared by dipping a 2"×8" glass plate into an aqueous dispersion (25% solids) of the debranched waxy maize starch, thereby causing a film to form on the glass plate. The glass plate was removed from the dispersion and allowed to dry at room temperature overnight. An opaque film was formed which, when resubmerged in water at room temperature, did not dissolve even when gently rubbed.

A similar film was prepared from the 85WF acid-converted waxy maize. After drying the film was clear. When resubmerged in water, the film dissolved.

EXAMPLE 6

This example illustrates that the starch of this invention may be used to form a stable, opaque or translucent cloud when dispersed in an aqueous medium.

Waxy maize starches and acid-converted (50WF) waxy maize starches were debranched by the method of Example 1 to the funnel viscosities listed in Table II.

Additionally, a tapioca starch was debranched by the method of Example 1 to a funnel viscosity of 54 seconds (10% solids). The tapioca dispersion was passed through a hand homogenizer before measuring transmittance. For comparative purposes, fully debranched, crystalline short chain amylose, prepared by the method claimed in U.S. Pat. No. 3,730,840, was dispersed in Waxy maize starches which had been debranched to yield 20 to 65% short chain amylose produced the most stable clouds. Fully debranched starch (U.S. Pat. No. 3,730,840) did not form a cloud.

EXAMPLE 7

This example illustrates that the starch of this invention may be used to form thermally reversible gels.

Waxy maize starches and acid-converted (50WF) waxy maize starches were debranched by the method of Example 1 to the funnel viscosities set out in Table III.

The following starches were also debranched by the method of Example 1 to the following funnel viscosities:

K. Acid-converted (50WF) tapioca—43.1 seconds (10% solids);

L. Tapioca-54.2 seconds (10% solids); and

M. Waxy maize/tapioca 80/20 blend—137 seconds (10% solids).

Additionally, for comparative purposes, fully debranched crystalline product was prepared by the method claimed in U.S. Pat. No. 3,730,840.

Thermally reversible gel forming properties of these starches were evaluated by dispersing 25 g, anhydrous, of starch in 75 g of distilled water. The dispersion was heated on a steam bath for 20 minutes, poured into a petri dish, refrigerated for one hour and subjectively evaluated for gel formation. The resulting gels were thermally reversible if they become fluid upon reheating on a steam bath and formed gel again upon standing at room temperature.

Results of gel evaluations are set forth in Table III. The material prepared by the method of U.S. Pat. No. 3,370,840 did not form a gel. Debranched waxy maize samples containing from about 30 to 64% short chain amylose formed thermally reversible gels. Similar gels were obtained from

TABLE III

| Starch[a] | Funnel Viscosity (seconds) | % Solids | % Short Chain Amylose | Gel Evaluation Initial | Thermally Reversible |
|---|---|---|---|---|---|
| Waxy Maize | | | | | |
| A | 27.6 | 10 | 13.5 | no gel[c] | — |
| B | 20.6 | 10 | 30 | gel[b] | Yes |
| C | 11.8 | 19 | 52 | gel[b] | Yes |
| D | 10.0 | 19 | 53.3 | gel[b] | Yes |
| E | 8.0 | 19 | 64 | gel[b] | Yes |
| Acid-Converted Waxy Maize (50 WF) | | | | | |
| F | 42 | 19 | 23 | no gel | — |
| G | 20.6 | 19 | 28 | soft gel[b] | — |
| H | 18.7 | 19 | 32 | gel[b] | Yes |
| I | 12.0 | 19 | 48 | gel[b] | Yes |
| J | 9.5 | 19 | 58 | gel[b] | Yes |
| Tapioca (50 WF) K | 43.1 | 10 | — | gel[b] | Yes |
| Tapioca L | 54.2 | 10 | — | soft gel[b] | No |
| Waxy Maize/Tapioca (80/20) M | 137 | 10 | — | gel[b] | Yes |
| Fully Debranched (U.S. Pat. No. 3,720,840) | — | — | 85 | paste no gel | — |

[a]See Example 8.
[b]Gels are cloudy, opaque, with fat-like texture and lubricity.
[c]Slightly cloudy paste.

debranching of acid-converted (50WF) waxy maize starch, acid-converted (50WF) tapioca starch and the 80/20 waxy maize/tapioca blend. Tapioca starch formed a gel which was not thermally reversible.

EXAMPLE 8

This example illustrates that the starch of this invention may be used to form high strength gels.

Corn starch was debranched by the method of Example 1 to the funnel viscosities set forth in Table IV and the starch dispersions were adjusted to 5 or 10% solids. Unmodified corn starch slurries were prepared and jet cooked by the method of Example 1. After cooking, the starch dispersions were adjusted to 5 or 10% solids. The control samples (unmodified corn starch) and the debranched samples prepared from starch A were refrigerated for 60 hours. The debranched samples B and C were refrigerated for one hour. Gel strength (grams) was measured with a Stevens L.F.R.A. Texture Analyser, employing a ½" diameter cylinder (Probe TA-5) at a speed of 0.5 mm/sec. Results are set forth in Table IV.

Unmodified corn starch did not form a gel at 5% solids. The 10% solids sample formed a very weak gel (9 grams). In contrast, all debranched corn starch samples formed very strong gels (175–550 grams) at 10% solids and strong gels at 5% solids (40–250 grams), even after only one hour of refrigeration.

TABLE IV

| Corn Starch Sample[a] | Caustic Funnel Viscosity[b] (seconds) | Gel Strength[d] (grams) 10% Solids | 5% Solids |
|---|---|---|---|
| Control | [c] | 9 | No gel |
| Debranched: | | | |
| A | 30 | 175 | 250 |
| B | 14 | 550 | 150 |
| C | 12 | 310 | 40 |

[a]See Example 8
[b]At 10% solids
[c]Viscosity of 10% solids corn starch control was too high to measure.
[d]Control and debranched starch A were refrigerated for 60 hours; debranched starches B and C for one hour, prior to measuring gel strength.

EXAMPLE 9

This example illustrates that a variety of starches may be employed in this invention.

The partial enzymatic debranching process of Example 1 was carried out on the following starches:

A. Corn starch debranched for 0, 1.0, 5.0 and 24.0 hours; and debranched to a 12 second (10% solids at 72° F.) funnel viscosity with 13 PUN of pullulanase/g starch;

B. Tapioca starch (21% solids) debranched for 0, 0.25, 1.0, 2.0 and 5.0 hours with 13 PUN of pullulanase/g starch; and C. Potato starch (18% solids) debranched for 0, 0.25, 1.0, 4.0 and 16.0 hours with 13 PUN of pullulanase/g starch.

The funnel viscosity and percent short chain amylose were measured by the methods set forth above. Subjective observations of starch characteristics were made by the methods described in Examples 4–7 above. An acid-converted (32WF) tapioca was also observed for comparative purposes. Results are set forth in Table V.

EXAMPLE 10

This example illustrates that a variety of partially debranched starch derivatives may be prepared by the process of this invention.

The derivatization reactions and the partial enzymatic debranching process were carried out as in Example 1 on the starches listed in Table VI.

Now that the preferred embodiments of the present invention have been described in detail, various modifications and improvments thereon will become readily apparent to those skilled in the art. Accordingly, the scope and spirit of the invention are to be limited only by the claims and not by the foregoing specification.

TABLE V

| Starch | Treatment Time (hrs.) | Funnel Viscosity | % Solids | % Short Chain Amylose | Subjective Observations Film | Gel[b] |
|---|---|---|---|---|---|---|
| Corn[a,c] | 0 | — | 10 | 0 | Soluble | soft opaque gel |
| Debranched | 1.0 | 97 | 10 | 14.5 | — | soft opaque gel |
| Debranched | 5.0 | 30 | 10 | 26.5 | Slightly soluble | slightly opaque gel |
| Debranched | 24.0 | 18 | 10 | 33.3 | — | opaque gel |
| Debranched | — | .12 | 10 | — | Insoluble | slightly opaque gel |
| Tapioca | 0 | | 21 | 0 | Translucent/soluble | None |
| Debranched | 0.25 | | 21 | 16 | Translucent/Redissolved | None/Rubbery |
| Debranched | 1.0 | | 21 | 25 | opaque/slightly soluble | Spongy paste/ with fluid |
| Debranched | 2.0 | | 21 | 36 | Translucent to opaque/ Insoluble | opaque gel |
| Debranched | 5.0 | | 21 | 45 | | |
| Acid/converted (32 WF) | | | 21 | | Translucent/soluble | None |
| Potato | 0 | | 18 | 0 | Translucent to slight/ cloud soluble | Paste/soft gel |
| Debranched | 0.25 | | 18 | 12 | Translucent to slight cloud/Partially soluble | Cloudy gel/ with fluid |
| Debranched | 1.0 | | 18 | 21 | opaque/Insoluble | Cloudy to opaque gel |
| Debranched | 4.0 | | 18 | 37 | opaque/Insoluble | opaque gel |
| Debranched | 16.0 | | 18 | 46.6 | — | opaque gel |

[a]Caustic Funnel Viscosity
[b]Gels are not thermally reversible
[c]Subjective observations and % short chain amylose measurements were conducted on different batches of debranched corn starch.

TABLE VI

| Starch | Treatment[b] | Reaction Time[c] (Hrs) | Funnel Viscosity (Seconds) | % Starch Solids |
|---|---|---|---|---|
| Waxy Maize | 0.5% OSA | 2.0 | 50 | 10 |
| " | 0.5% OSA | 1.5 | 47 | 10 |
| " | 0.5% OSA | 0.5 | 38 | 10 |
| " | 0.5% OSA | 1.0 | 25 | 10 |
| " | 0.5% OSA | 24.0 | 13 | 19 |
| " | 1.0% OSA | 24.0 | 12 | 19 |
| " | 1.0% OSA | 20.0 | 12 | 19 |
| " | 1.0% OSA | 2.0 | 50 | 10 |
| " | Acid-converted 50 WF | 20.0 | 9.8 | 19 |
| " | Crosslinked | 3.0 | 15 | 10 |
| " | Crosslinked | 3.0[d] | 10 | 10 |
| " | Crosslinked | 0 | over 200 | 10 |
| Corn[a] | 0.5% OSA | 3.0 | 63 | 10 |
| " | 0.75% OSA | 1.5 | 52 | 10 |
| " | 0.5% OSA | 1.5 | 49 | 10 |
| " | 0.5% OSA | 1.0 | 41 | 10 |
| " | 0.75% OSA | 1.5 | 36 | 10 |
| " | 3.0% Acetate | 2.5 | 40 | 10 |
| " | 3.0% Acetate | 0 | over 200 | 10 |
| Tapioca | 0.5% OSA | 3.5 | 65 | 10 |
| " | 0.5% OSA | 5.0 | 44 | 10 |
| Potato | 0.5% OSA | 1.0 | 65 | 10 |
| " | 1.0% OSA | 1.0 | 65 | 10 |
| " | 0.5% OSA | 2.0 | 25 | 10 |
| " | 1.0% OSA | 2.0 | 25 | 10 |

[a]Caustic funnel viscosity
[b]Percentages indicate percent reagent utilized on starch dry weight basis
[c]Duration of pullulanase treatment
[d]An additional 15 mls of pullulanase was added to the starch dispersion.

I claim:

1. Enzymatically debranched starch in powdered form, comprising up to 80%, by weight, short chain amylose and at least 20%, by weight, partially debranched amylopectin, which starch is capable of forming a thermally reversible gel, or a high strength gel, or a stable, opaque cloud, or a lubricating, fat-like texture, or a combination thereof in an aqueous dispersion.

2. The enzymatically debranched starch of claim 1, further comprising long chain amylose, amylopectin, or a combination thereof.

3. The enzymatically debranched starch of claim 1, wherein the starch is a waxy maize starch or amylopectin.

4. The enzymatically debranched starch of claim 1, wherein the enzymatically debranched starch comprises sufficient short chain amylose to form a water-insoluble film.

5. The starch of claim 1, wherein an alpha-1,6-D-glucanohydrolase, selected from the group consisting of pullulanase and isoamylase, is employed to partially debranch the starch.

6. The starch of claim 1, wherein the starch is modified by derivatization, by conversion or by crosslinking.

7. The enzymatically debranched starch of claim 1, comprising from 5 to 80%, by weight, short chain amylose and from 20 to 95% by weight, of a mixture of amylopectin and partially debranched amylopectin.

8. The enzymatically debranched starch of claim 1, comprising from 30 to 70%, by weight, short chain amylose and from 70 to 30%, by weight, of a mixture of amylopectin and partially debranched amylopectin.

9. An aqueous dispersion, comprising the enzymatically debranched starch of claim 1 in an amount effective to form a thermally reversible gel, wherein the enzymatically debranched starch comprises 25 to 70%, by weight, short chain amylose.

10. An aqueous dispersion, comprising the enzymatically debranched starch of claim 1 in an amount effective to form a gel having a lubricating, fat-like texture, wherein the starch comprises 25 to 70%, by weight, short chain amylose.

11. An aqueous dispersion, comprising the enzymatically debranched starch of claim 1 in an amount effective to form a gel having a Stevens L.F.R.A. Texture Analyser Probe TA-5 gel strength of at least 100 grams at 0.5/mm/sec, wherein the enzymatically debranched starch comprises 20 to 45%, by weight, short chain amylose.

12. A method for preparing partially debranched starch which is capable of forming a thermally reversible gel, or a high strength gel, or a stable, opaque cloud, or a lubricating, fat-like texture, or a combination thereof in an aqueous dispersion, comprising the steps of:
  (a) providing a pregelatinized starch;
  (b) hydrolyzing the alpha-1,6-D-glucosidic bonds of the starch with an alpha-1,6-D-glucanohydrolase until the starch comprises up to 80%, by weight, short chain amylose and at least 20%, by weight, partially debranched amylopectin; and
  (c) recovering the starch in a powdered form.

13. The method of claim 12, wherein the starch is debranched until the starch comprises from 5 to 80%, by weight, short chain amylose and from 95 to 20%, by weight, of a mixture of amylopectin and partially debranched amylopectin.

14. The method of claim 12, wherein the starch is debranched until the starch comprises from 30 to 70%, by weight, short chain amylose and from 70 to 30%, by weight, of a mixture of amylopectin and partially debranched amylopectin.

15. The method of claim 12, wherein the alpha-1,6-D-glucanohydrolase is a alpha-1,6-D-glucanohydrolase selected from the group consisting of pullulanase and isoamylase.

16. The method of claim 12, wherein the starch is modified by derivatization, by conversion or by crosslinking.

17. The method of claim 12, wherein the starch is debranched until sufficient short chain amylose is cleaved to form a water-insoluble film.

18. An aqueous dispersion, comprising debranched starch prepared by the method of claim 12 in an amount effective to form a thermally reversible gel, wherein the starch comprises 25 to 70%, by weight, short chain amylose.

19. An aqueous dispersion, comprising debranched starch prepared by the method of claim 12 in an amount effective to form a gel having a lubricating fat-like texture, wherein the starch comprises 25 to 70% by weight, short chain amylose.

20. An aqueous dispersion, comprising debranched starch prepared by the method of claim 12 in an amount effective to form a gel having a Stevens L.F.R.A. Texture Analyser Probe TA-5 gel strength of at least 100 grams at 0.5/mm/sec, wherein the starch comprises 20 to 45%, by weight, short chain amylose.

* * * * *